(12) United States Patent
Rönnholm

(10) Patent No.: US 7,248,915 B2
(45) Date of Patent: Jul. 24, 2007

(54) NATURAL ALARM CLOCK

(75) Inventor: Valter A. G. Rönnholm, Turku (FI)

(73) Assignee: Nokia Corporation, Espoo (FI)

( * ) Notice: Subject to any disclaimer, the term of this patent is extended or adjusted under 35 U.S.C. 154(b) by 392 days.

(21) Appl. No.: 10/789,417

(22) Filed: Feb. 26, 2004

(65) Prior Publication Data

US 2005/0190065 A1  Sep. 1, 2005

(51) Int. Cl.
*A61B 5/00* (2006.01)
(52) U.S. Cl. .................. 600/544; 340/575; 600/300
(58) Field of Classification Search ............... 600/300, 600/544; 340/575
See application file for complete search history.

(56) References Cited

U.S. PATENT DOCUMENTS

| | | | | |
|---|---|---|---|---|
| 4,228,806 | A * | 10/1980 | Lidow | 600/544 |
| 4,617,525 | A * | 10/1986 | Lloyd | 340/573.1 |
| 4,776,345 | A | 10/1988 | Cohen et al. | |
| 5,101,831 | A * | 4/1992 | Koyama et al. | 600/500 |
| 5,507,716 | A | 4/1996 | LaBerge et al. | |
| 5,928,133 | A | 7/1999 | Halyak | |
| 5,999,846 | A * | 12/1999 | Pardey et al. | 600/544 |
| 6,322,515 | B1 | 11/2001 | Goor et al. | |
| 6,497,658 | B2 * | 12/2002 | Roizen et al. | 600/301 |
| 6,888,779 | B2 * | 5/2005 | Mollicone et al. | 368/10 |
| 6,945,935 | B1 * | 9/2005 | Sasse et al. | 600/300 |
| 2002/0002326 | A1 * | 1/2002 | Causey et al. | 600/300 |
| 2002/0019584 | A1 * | 2/2002 | Schulze et al. | 600/300 |
| 2002/0080035 | A1 | 6/2002 | Youdenko | |
| 2003/0032866 | A1 * | 2/2003 | Winter et al. | 600/300 |
| 2003/0095476 | A1 * | 5/2003 | Mollicone et al. | 368/250 |
| 2004/0073098 | A1 * | 4/2004 | Geva et al. | 600/300 |
| 2005/0043652 | A1 * | 2/2005 | Lovett et al. | 600/595 |
| 2005/0080349 | A1 * | 4/2005 | Okada et al. | 600/534 |
| 2005/0101841 | A9 * | 5/2005 | Kaylor et al. | 600/300 |
| 2006/0020178 | A1 * | 1/2006 | Sotos et al. | 600/300 |

FOREIGN PATENT DOCUMENTS

| | | |
|---|---|---|
| DE | 42 09 336 A1 | 9/1993 |
| DE | 43 03 933 A1 | 8/1994 |

(Continued)

OTHER PUBLICATIONS

"Stage at Awakening, Sleep Inertia and Performance", C. Cavallero et al, "Sleep Research Online" 5(3): 89-97, 2003, via the internet.

(Continued)

*Primary Examiner*—Charles A. Marmor, II
*Assistant Examiner*—Karen E Toth

(57) ABSTRACT

A mobile terminal is presented, having capability to determine when a user should be stimulated toward an awake state. The terminal includes a receiver for receiving a sleep descriptor signal indicative of at least one sleep characteristic of the user, and also includes a signal processing module for processing the sleep descriptor signal. The signal processing module is arranged to provide, at least partly in response to the sleep descriptor signal, a stimulation signal indicative that the user should be stimulated. The mobile terminal is also usable for communication by the user in the awake state. This invention further includes a method, system, and monitor to be used with the mobile terminal in order to stimulate the user toward an awake state.

25 Claims, 4 Drawing Sheets

FOREIGN PATENT DOCUMENTS

| | | |
|---|---|---|
| DE | 196 42 316 A1 | 4/1998 |
| DE | 199 16 944 A1 | 10/2000 |
| EP | 0 496 196 A1 | 7/1992 |
| EP | 1 059 575 A2 | 12/2000 |
| EP | 1 163 877 A1 | 12/2001 |
| FR | 2 597 995 | 10/1987 |
| FR | 2 634 913 | 2/1990 |
| FR | 2 665 080 | 1/1992 |
| JP | 9-264977 | 10/1997 |
| JP | 2000-316832 | 11/2000 |
| JP | 2001-17550 | 1/2001 |
| JP | 2001-116866 | 4/2001 |
| JP | 2001-242268 | 9/2001 |
| JP | 2002-372593 | 12/2002 |
| KR | 2001-0095796 | 11/2001 |
| KR | 10-0321532 | 1/2002 |

OTHER PUBLICATIONS

"Picking REM from Finger: An Automatic Algorithm to Identify REM Sleep Based on Measurements of Peripheral Arterial Tone", P. Lavie et al, SLEEP, vol. 26, Abstract Suppl 2003.

"Disappearance of Sleep Inertia is Associated with Distal Vasoconstriction", K. Kräuchi et al, SLEEP, vol. 26, Abstract Suppl. 2003.

\* cited by examiner

NATURAL ALARM CLOCK

FIELD OF THE INVENTION

The invention relates to mobile communication devices, and more particularly to mobile devices that are equipped to operate as alarm clocks.

BACKGROUND OF THE INVENTION

A phenomenon known as "sleep inertia" often manifests itself after a person wakes up. This is a common problem, especially if the person did not get enough sleep, or was awoken abruptly, or was awoken from a deep sleep. A person with sleep inertia might demonstrate all the outward physical signs of being awake, and yet not be cognitively awake. Symptoms of sleep inertia include impairment of performance and reaction time when thinking or using motor skills, reduction in memory, and impairment of decision-making ability. Sleep inertia causes many people to function poorly without ritual intake of caffeine, which may alleviate the condition. Sleep inertia can also be dangerous for people who drive in the early morning hours shortly after waking.

Sleep patterns vary from person to person, but everyone attains several different stages of sleep each night. These stages are generally broken down into NREM sleep, or Non-Rapid Eye Movement sleep and REM sleep, or Rapid Eye Movement sleep. NREM is a deeper sleep than REM sleep in certain respects. The deepest stages of NREM sleep (called stages 3 and stage 4 sleep) usually occur during the hours after going to sleep, instead of in the morning hours before waking up. It is very advantageous to wake up gradually instead of abruptly, and to wake up during or shortly after a period of REM sleep instead of during deeper NREM sleep, in order to reduce sleep inertia. In general, it can be much more pleasant to wake up in this natural manner.

Waking up is especially problematic for travelers between time zones, who are susceptible to jet lag and the like. In contrast, people who get a good night's sleep at home are not likely to be in a deep NREM sleep when they wake, but even for them it can be advantageous to wake up slowly and in REM sleep or near a transition from REM to NREM sleep, instead of waking abruptly or from an NREM sleep that is not near a transition from REM sleep.

It is known to use telephones for purposes of waking people up. For example, many hotels offer wake-up calls to their customers, which eliminates the need for a traveler to take along an alarm clock. However, these typical wake-up systems arouse a person at a specific requested time, instead of when the user is in an appropriate sleep stage. Even if sleep sensors were made available to hotel guests, the hotel would be vulnerable to theft of those sensors. Moreover, a normal hotel visitor would dislike attaching unfamiliar sensors to his or her body at night, including sensors which would have been used by another guest the previous night. No solution has yet been devised to combine the convenience of telephonic wake-up with the benefits of waking up in an appropriate sleep stage.

There are various ways to use sensors in order to detect REM sleep. During REM sleep, the heart rate and cardiac output increase compared to NREM sleep, and therefore heart rate sensing can be used to estimate when REM sleep is occurring. Also, during REM sleep, the physiological functions regulating body temperature are inactive, and the body temperature may thus rise or fall, depending on the ambient temperature. Sweating and shivering is practically nonexistent but may occur if the ambient temperature is extreme. Also, body movements are inhibited during REM sleep.

Another indicator of REM sleep is blood vessel constriction (vasoconstriction) that can be measured, for example, in the hands and feet. Blood flow in the arterioles and capillaries of the extremities decreases sharply during REM sleep, due to vasoconstriction, and this can be measured, for example, using Peripheral Arterial Tone (PAT) measurement, as described by Goor et al. (U.S. Pat. No. 6,322,515). An algorithm presented by Lavie et al. in SLEEP, Vol. 26, Abstract Supplement (2003), p. A385–A386 may be used to detect REM sleep with the aid of PAT measurement Another way to detect REM is by directly sensing eye movement, as disclosed by Laberge et al. (U.S. Pat. No. 5,507,716). Laberge discloses a comfortably worn face mask covering face portions, and a headband supporting the face mask about the person's head. The face mask, in turn, supports components of this equipment, which sense a person's eyelid movements during sleep. The sensing components supported on the face mask utilize a low level infrared emitter positioned on the face mask to direct infrared light to the eyelid of a sleeping person, and also utilize a low level infrared detector to receive the reflections of this infrared light from the surface of the eyelid of the sleeping person. The Laberge invention is directed at enhancing dreams, and therefore includes other features in addition to the REM detecting components. It is noted that many people already wear an eye mask (also called a sleep mask or blindfold) when going to sleep, in order to keep out light, and those existing eye masks may also keep out sound and/or provide soothing sound.

Alarm clocks correlated to REM have been devised, but the existing art does not address certain problems. The main problem with the prior art solutions is that they are inconvenient to take along when travelling. However, sleep deprivation and disturbances of the circadian rhythm (i.e., disturbances of a person's internal 24-hour biological clock) are very common when travelling, due to jet lag, fragmentary sleep, and long travel times. The need for a natural alarm clock is thus even greater when travelling. The problem of the prior art solutions is thus their practical immovability. They can of course be moved but they are rather large and heavy to take along when travelling. Most prior art solutions include a central unit, and the natural alarm clock is thus comparably bulky, especially for people preferring to travel light (e.g., with cabin baggage only).

Alarm clocks correlated to REM are referred to here as natural alarm clocks. The existing natural alarm clocks fall into several categories. Natural alarm clocks based on electroencephalography (EEG) measurements include Lidow (U.S. Pat. No. 4,228,806), Krischenowski (DE19642316), Cohen et al. (U.S. Pat. No. 4,776,345), Schroeder (EP0496196), Choi (KR2001095796), and Aizawa (JP9264977). Natural alarm clocks based on heart rate include Koyama et al. (U.S. Pat. No. 5,101,831), Bae et al (KR321532), Knutzen et al. (DE4209336), and Westerfeld (DE19916944). Natural alarm clocks based on temperature or skin resistance measurement include Youdenko (US2002/0080035), Halyak (U.S. Pat. No. 5,928,133), and Matsuura (JP2001017550). Natural alarm clocks based on accelerometers include Barron et al. (EP1163877), Watanabe et al. (JP2002372593), and Yanai et al. (JP2000316832). Natural alarm clocks based on Static Charge Sensitive Beds (SCSB) include Pellet (FR2665080). Natural alarm clocks based on muscle signals detected using electromyography (EMG) include Boucheron (FR2634913). Other natural alarm clocks include Masuda et al. (EP1059575), Boucheron (FR2597995), Yoshida (JP2001242268), Miura (JP2001116866), and Beno (DE4303933).

The cause of sleep inertia is not totally clear. Heart and respiratory rate decrease during NREM sleep, the activity of the sympathetic nervous system is low, distal blood vessels are relatively dilated, and blood pressure is decreased. These facts imply that the cerebral blood flow is relatively low. The decreased respiratory rate may also imply that the oxygen saturation of the blood is relatively low and/or the carbon dioxide saturation relatively high, so the oxygen levels of the brain may be relatively low and the carbon dioxide levels correspondingly high. The brain is also in a passive state during NREM sleep. In contrast, during REM sleep, heart and respiratory rate and blood pressure are variable and increased compared to NREM sleep, and vasoconstriction occurs as a result of increased sympathetic nervous activity. These facts seem to suggest that cerebral blood flow is relatively high during REM sleep, compared to NREM sleep. The increased respiratory rate seems to suggest that the oxygen saturation level of the blood is relatively high during REM and the carbon dioxide saturation level of the blood is correspondingly relatively low compared to NREM sleep. It thus seems probable that the oxygen levels of the brain would be higher at the end of a REM sleep stage than during the end of a longer NREM stage or at the beginning of a REM stage. According to a similar reasoning, the carbon dioxide levels of the brain would be relatively low at the end of a REM sleep stage compared to the end of an NREM sleep stage or the beginning of a REM sleep stage. In addition, the brain is in a highly active state during REM sleep. These findings seem to suggest that the operational premises of the brain are better at the end of an REM sleep stage than at the end of a longer period of NREM sleep or at the beginning of a REM sleep stage.

Kräuchi et al. suggest a correlation between distal vasoconstriction and sleep inertia in their abstract in SLEEP, Vol. 26, Abstract Supplement, 2003 p. A56–A57. This seems to suggest that it would be beneficial to use a vasoconstriction related measurement as a sleep characteristic measurement.

As previously discussed, some examples of sleep characteristics are: heart rate information; heart rate variability information; ECG (electrocardiography) signals; EEG (electroencephalography) signals; respiratory rate information; respiratory rate variability information; vasoconstriction or vasodilatation measurement signals such as PAT (peripheral arterial tone), PPG (photoplethysmography), PTT (pulse transit time), or IPG (impedance plethysmography) signals, or variation information regarding PAT, PPG, PTT and/or IPG; body temperature and/or distal temperature information; blood pressure information; and actigraphy, accelerometer, or movement sensor information, with or without sleep stage or depth information.

SUMMARY OF THE INVENTION

The problems of the prior art are solved by exploiting the processing power, operating system and/or user interface of a mobile terminal (e.g., mobile phone, pager, personal digital assistant, laptop computer, device connectable to a local, regional, national or global network, other compact or portable phone, et cetera). For example, this solution solves the problem described above of hotel visitors having to use sensors provided by the hotel. More generally, instead of using a stand-alone central unit for a natural alarm clock, the existing capabilities of a mobile terminal are used. All that is needed is, for example, a headband or wrist band with a sensor system for sensing the sleep stages of the user, along with a short distance (e.g., Bluetooth) interface for transferring the measurement data to the mobile terminal. The mobile terminal then functions as the "central unit" of the natural alarm clock and takes care of its functionalities (for example, alarming, user interface, signal processing, sleep stage detection, alarm functionalities, and the like).

The prior art does not suggest a natural alarm clock that is sufficiently movable in order to conveniently take along when travelling. In addition to not recognizing the travel problem, the prior art does not suggest solving that problem by using the capacities of a mobile terminal to reduce the bulk (and cost) of the other parts of the natural alarm.

The REM information can be used not only for timing the alarm, but also for providing biofeedback to enhance sleep, such as by providing soothing sounds until the user passes from REM sleep into NREM sleep. Likewise, since it is advantageous to wake up a person gradually, and to do so from shallower NREM sleep than deeper NREM sleep, the present natural alarm can be used to first very gently bring the user, who has been in NREM sleep for a certain time, from deeper NREM sleep into shallower NREM sleep, and then once the user is in shallower NREM sleep the alarm can be substantially increased in order to wake the user up. Furthermore, for a user wishing to sleep lightly so that he will be able to awake at any time without risk of severe sleep inertia, the present invention is useful for providing a slight stimulus to prevent the user from slipping into a deeper NREM sleep, without actually waking the user up.

The present invention is also very useful for handling incoming calls to the mobile terminal. An incoming call may come from a wireless network, or via a direct (e.g., Bluetooth) connection in an adjacent room. In either case, the person calling may be allowed to wake up the user if the user is in a suitable phase of sleep, but be denied immediate access to the user if the user is in an unsuitable phase of sleep. However, the person calling may be allowed to leave an urgent message which will be delivered when the user reaches a suitable stage of sleep.

Moreover, if the user is wearing a headband equipped with an REM sensor system, then it is possible for the user to wear the headband over his or her ears, and thus the headband can be equipped with earpieces that may keep out noise, and/or the earpieces can also provide audio for helping the user go to sleep, and/or for preventing the user from sinking into deep NREM sleep, and/or for waking the user up, and/or for preventing the user from going to sleep. These audio earpieces could be used in public spaces, without disturbing other people. The headband and earpieces can also be used as a hands-free way for the user to hear incoming phone calls, while the user is awake. When the user wants to go to sleep, it will be possible for the user to pull the headband over his eyes to keep out light, and so the headband can be equipped with eye pads, which may or may not be able to directly detect eye movement, and may or may not be able to provide visual stimuli when it is time for the user to wake up.

The present invention utilizes short distance wireless communication such as Bluetooth, which ensures that a person who is having his or her sleep monitored will be able to move freely without attached wires or the like. Moreover, since Bluetooth only transmits over short ranges, the power requirements are small, and so the sleep sensors attached to a person will not require bulky battery packs, or batteries which must be frequently recharged. Bluetooth is in simple terms a better wireless technology than Infrared. IR communications, which are common in television remote control devices, need what is called line-of-sight. Bluetooth, on the other hand, is a high-speed, short distance wireless technology in the 2.4 GHz spectrum. Bluetooth has three power specifications: class 3 Bluetooth is capable of transmitting 10 cm or 4 inches, class 2 Bluetooth is capable of transmitting 10 m or 33 feet, and class 1 Bluetooth is capable of transmitting 100 m or 300 feet. As Bluetooth uses a radio frequency, it is capable of passing through walls and other objects. All of these Bluetooth classes are capable of a 1 megabits per second transmission rate. The next generation of Bluetooth technology is anticipated to be in the region of a 2 to 12 megabits per second transmission rate. Class 1 and 2 Bluetooth are especially suited for mobile phones, modems, and the like because of low power consumption (Class 2 Bluetooth devices are currently much more common than Class 1 devices). Combining a Bluetooth or similar technology with a mobile terminal and sleep sensors can dramatically improve present technologies for waking up.

According to this invention, a mobile terminal has capability to determine when a user should be stimulated toward an awake state. The terminal includes a receiver for receiving a sleep descriptor signal indicative of at least one sleep characteristic of the user, and also includes a signal processing module for processing the sleep descriptor signal. The signal processing module is arranged to provide, at least partly in response to the sleep descriptor signal, a stimulation signal indicative that the user should be stimulated. The mobile terminal is also usable for communication by the user in the awake state. This invention further includes a method, system, monitor, and software to be used with the mobile terminal in order to stimulate the user toward an awake state.

The electronic monitor of the present invention is for reporting sleep status of a mobile terminal user, and the electronic monitor includes a sensor responsive to at least one physiological manifestation indicating a characteristic of sleep. The sensor provides a sleep characterizing signal, and a transmitter in the electronic monitor is responsive to the sleep characterizing signal. The transmitter is for providing a sleep descriptor signal to the mobile terminal, and the sleep descriptor signal is wireless with a frequency obviating line of sight contact between the electronic monitor and the mobile terminal.

An electronic device according to the present invention may be entirely wearable on the human body, but the user interface could significantly increase its size and therefore make the electronic device uncomfortable when sleeping. This problem (which is apparent in prior art such as Bae) can be solved by the user interface being provided by a mobile terminal separate from the worn device, so that the mobile terminal will be used to send control data to the worn device.

The present invention includes a computer-readable medium for use in the mobile terminal, the medium being encoded with a software data structure for determining, based at least upon a sleep descriptor signal, when to stimulate the user to bring the person toward an awake state.

The invention further includes an electronic device for bringing the user toward an awake state, this electronic device being more self-contained than the previously described electronic monitor. The electronic device includes a sensor that is responsive to a physiological manifestation indicative of a sleep characteristic. The sensor is arranged to create a sleep characterizing signal representing the sleep characteristic. A signal processing module in the electronic device processes the sleep characterizing signal, and includes circuitry or software or both. The signal processing module is arranged to detect a suitable instant for providing a stimulation signal that will cause the user to come toward the awake state. The electronic device further includes a stimulation module or unit, responsive to the stimulation signal, for creating a jarring signal for bringing the user toward the awake state; for example, the stimulation unit may include an audio device for stimulating the user, and this same audio device can be configured to also provide an awake user with sounds of a call incoming to the mobile terminal. The stimulation module includes circuitry or software or both. This electronic device is wearable on a human body, and the stimulation signal is graduated, so that the user will not be awoken abruptly.

Additionally, the invention includes a method for determining when a user should be stimulated toward an awake state. This method includes receiving a sleep descriptor signal indicative of a sleep characteristic of the user, processing the sleep descriptor signal, and providing, in response to the sleep descriptor signal, a stimulation signal indicative that the user should be stimulated. This method is performed within a mobile terminal that is also usable by the user in the awake state, for communicating via a wireless network.

Moreover, the present invention includes a system for bringing a user of a mobile terminal toward an awake state. The system includes a sensor responsive to a physiological manifestation that indicates a characteristic of sleep. The sensor provides a sleep characterizing signal. The system also includes a transmitter, responsive to the sleep characterizing signal, the transmitter being for providing a sleep descriptor signal to the mobile terminal. The system further includes a receiver at the mobile terminal for receiving the sleep descriptor signal, and a signal processing module at the mobile terminal for processing the sleep descriptor signal. The signal processing module is arranged to provide, at least partly in response to the sleep descriptor signal, a stimulation signal indicating that the user should be stimulated toward the awake state. The mobile terminal is also usable by the user when he or she is awake, for communication purposes.

DETAILED DESCRIPTION OF THE INVENTION

Figure 1A:
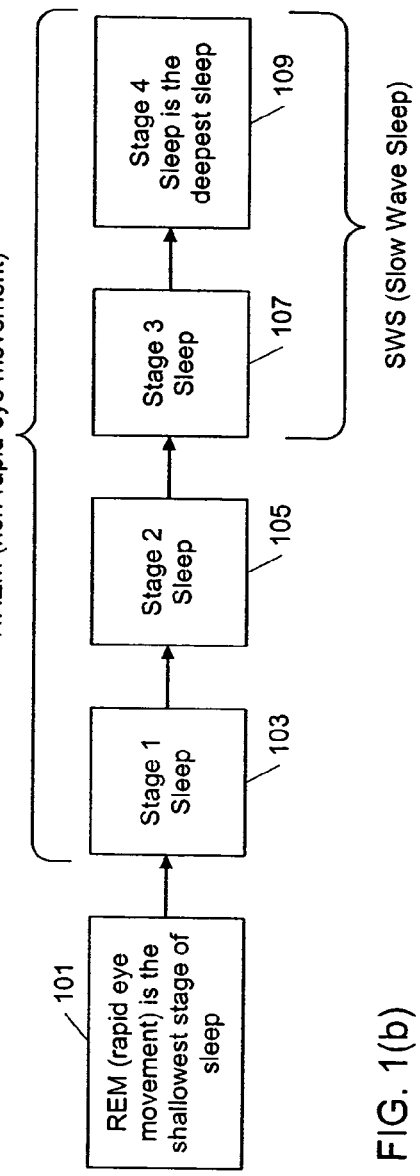
FIG. 1(a) is a block diagram showing the different sleep stages as determined by sleep research.

There are four basic sleep stages during NREM, as illustrated in FIG. 1(a) which will be referred to more extensively later in this specification. Stage 1 sleep is a transitional phase between wakefulness and sleep or between REM sleep and deeper NREM sleep. Brain waves become smaller and slower. In this stage, a person is still easily awakened and might even deny having slept. Stage 2 sleep is a deeper, intermediate stage of sleep and occupies about 50 per cent of an adult's sleep pattern. In this stage, blood pressure, metabolism and cardiac activity decrease.

Brain waves are larger with occasional bursts of activity. A person will not see anything even if the eyes are opened, however, can easily be awakened by sound. Stage 3 sleep is the beginning of deep sleep and is characterized by delta waves—slow brain waves which are about five times the size of brain wave patterns in stage 2 sleep. A person will be far more difficult to awaken during this stage. Stage 4 sleep is when the deepest sleep occurs and is characterized by large delta brain waves. If the person is a sleepwalker or a bed wetter, these activities will begin in this phase. Waking someone from Stages 3 and 4 sleep is quite difficult. A person awakened from these deep sleep stages will probably be groggy, disoriented and confused and experience heavy sleep inertia. Stages 3 and 4 are referred to as slow wave sleep (SWS).

Some research seems to suggest that it would be better to wake up right after a phase of REM sleep rather than during the REM sleep. Thus, a device preferably wakes up a user at a suitable point in time, either during REM sleep or at (or near) a transition from REM to NREM sleep.

A sleeping person may move from NREM sleep to wakefulness without passing through REM. In other words, a sleeping person being slightly aroused by a sound may go through the following sequence: stage2→awake→stage2. Such a transition may be a reaction to a sound, but may also occur without any exterior causes. Thus, it may not be possible to bring a person to REM sleep by generating external stimuli.

REM sleep differs remarkably from NREM sleep. The conclusion that REM sleep is the shallowest sleep stage is not unambiguously correct. Even though many of REM sleep's characteristics resemble wakefulness, other characteristics imply that REM sleep is in some sense deeper than NREM sleep. A person is actually paralyzed during REM sleep (nature's way to make sure that we don't hurt ourselves when our brain reacts to our dreams). This neurological paralysis functionality does not occur during NREM sleep. Sometimes people may move when they dream but that is actually an unusual state in which one part of the brain is believed to be awake while another part is asleep. The sensory impulses (touch, sound, et cetera) are also inhibited to some extent during REM. The threshold for reacting to a sound is actually higher for REM than for shallow NREM.

When a person falls asleep, he or she typically goes through the following initial sequence of sleep stages: awake→stage 1→stage 2→stage 3→stage 4→stage 3→stage 2 (→stage 1)→REM (→stage 1)→stage 2. That is, the first REM-stage occurs about 70–80 minutes after sleep onset. Another thing to realize is that it is possible to move from stage 2 to REM or vice versa without "passing through" a phase of stage 1. This is true for other transitions as well, but stage 1 is often "left out" when "going into" or "coming out of" REM sleep. Stage 1 is thus often associated with falling asleep.

As mentioned, REM sleep differs greatly from NREM sleep in several respects. Although REM sleep is usually not subdivided into substages, tonic (persistent) and phasic (intermittent) aspects of REM sleep are often distinguished. During REM sleep, the body is practically paralyzed, and so the signals created in the brain when dreaming are not conveyed to the muscles. However, twitching or spasm of a muscle or a group of muscles (myoclonus) may occur. Moreover, during REM sleep, sensory input is damped, which means that the senses are less sensitive, and thus sound and touch sensitivity is decreased. The arousal or awakening threshold is higher during REM sleep than in other sleep stages.

During NREM sleep, particularly SWS, there is a reduction in physiological activity; metabolism, heart rate and respiratory rate are decreased. This contrasts with phasic REM sleep, in which breathing becomes irregular, heart rate increases and becomes more variable, and blood pressure shows transient elevations.

During NREM sleep, the body temperature drops and sweating and shivering diminishes. In contrast, during REM-sleep, thermoregulation is nonexistent, and thus the body temperature may slightly drift from the body temperature on REM onset.

The phenomenon of sleep inertia is typically worst when awakening from SWS, but SWS usually occurs in the few hours after going to sleep, instead of occurring in the morning hours before waking. Still, sleep inertia tends to be worse if one awakes during a deeper sleep stage as compared to waking from a lighter sleep, and the best time to wake appears to be near or during the transition from REM sleep to NREM sleep.

The present invention can be embodied as a combination of a sensor unit and a central unit. The sensor unit can be, for example, a head-, chest- or wristband. The central unit can be, for example, a mobile terminal such as a mobile phone, laptop computer or palmtop device.

A simple embodiment of the invention is a head-, chest- or wrist-band comprising sensors, a processing unit (hereinafter also called a signal processing module), a power source and an awakening apparatus (hereinafter also called an awakening unit or awakening module). The sensors can be EEG-electrodes, EMG-sensors, a heart rate sensor, blood pressure sensor, body temperature sensor, skin resistance sensor, Peripheral Arterial Tone (PAT) sensor, photoplethysmography (PPG) sensor, and/or a static charge sensitive bed (SCSB). The sensors can also be any other sensor capable of measuring a magnitude correlating with the characteristics of sleep. The processing unit can be a microcontroller, embedded system, or some other combination of circuitry and/or software.

The processing unit processes the measured signals. It may, for example, detect that REM stage sleep is present by measuring the variations in heart rate, the variations in breathing, or the variations in the level of vasoconstriction. A transition from REM to NREM may then be determined by detecting a lasting decrease in these variations. For example, if an even heart rate is measured for a certain time (e.g., 3, 5 or 7 minutes) after a period of significant variations in the heart rate, it can be determined that a transition from REM to NREM has occurred or is occurring. Alternatively, the algorithm presented by Lavie et al in SLEEP, Vol. 26, Abstract Supplement, 2003 p. A385–A386 may be used to detect REM sleep with the aid of PAT measurement. The apparatus may also comprise a user interface for letting the user enter a desired time of waking up. The time may be entered as an interval (e.g. between 6:30 and 7:30). The processing unit can maintain a clock and check whether the current time is within the set interval each time an REM/NREM-transition is detected, and alternatively, the detection can be activated when this interval begins. If a transition is detected within such an interval the processing unit activates the awakening unit. The awakening unit may be a loudspeaker or buzzer or other device causing an audible alarm. It may also be a vibrator causing a vibrating alarm. Alternatively, the awakening apparatus may be a transmitter capable of transmitting a signal that causes an external device to activate an alarm. In this case the central unit functions basically as an alerting device. However, the central unit may provide additional functionalities such as an enhanced user interface and/or a memory for storing sleep history data, which can then be viewed later by the user or used for preparing and maintaining a mathematical model of the circadian cycle of the user. The sensor unit may have a simple user interface, for example a four-digit LCD display and a few keys for setting the time and the alarm interval (which may be a standard length interval ending at a time inputted by the user). The enhanced user interface of the central unit may be a larger and more sophisticated display and with a larger keypad. The enhanced user interface may provide the user with more detailed information of his/her sleep history, for example as a hypnogram (i.e., sleep phase diagram) or present his/her approximate sleep debt in minutes and hours. The interval may be set more freely. The central unit may also be used to send the data to a third device such as a personal computer or database for storage, monitoring, modelling or other purposes. The device of the present invention may, for example, be set to stimulate or awaken the user within a set interval if either REM sleep is detected, or REM sleep is detected for at least a certain period of time (e.g. 5, 10, 15 or 20 minutes), or a transition from REM to NREM is detected.

Another embodiment of the invention is a sensor unit comprising a head-, chest- or wrist-band comprising sensors, a processing unit and a transmitter. The sensors may be similar to the previous example. The processing unit can be a micro controller, embedded system, or some other combination of circuitry and/or software. The transmitter may be a bluetooth transmitter or other short-range radio transmitter. The transmitter sends data to a central unit such as a mobile terminal. The processing can be divided in many different ways between the sensor unit and the central unit. One way to divide the signal processing is to perform minimal signal processing in the sensor unit and let the central unit perform most of the signal processing. The processing unit can, for example, simply prepare the measured signals for transmission (e.g., amplification and A/D-conversion). Alternatively, the sensor unit can perform most of the signal processing, wherein only an indication to sound off an alarm may be transmitted to the central unit (the central unit may trigger a vibrating alarm at a separate third device by a radio signal). Any other division of the signal processing between the sensor unit and the central unit is possible. The sensor unit may detect REM/stage 1-transitions and transmit indications of these, whereas the central unit provides a user interface, approximates the sleep cycles, estimates the amount of sleep debt the user is suffering from, and determines a suitable time to wake up the user. Alternatively, the sensor unit may determine the entropy of the measured signals, and transmit this data to the central unit at a suitable rate. Or, the sensor unit may detect the different sleep stages and transmit this data (awake/REM/stage1/stage2/stage3/stage4 or simply REM/"deeper sleep") to the central unit, whereas the central unit then determines the suitable time to awaken the user and/or, e.g., uses this data to maintain a statistical or mathematical model of the user's sleep and/or circadian cycles and amount of sleep debt. The transmission rate can also vary. The central unit may only send data when the time interval defined by the user approaches (e.g., if the time interval is 6:30 to 7:30, the sensor unit may begin to send measurement data from 5:30 onwards). Alternatively, data may be sent at a lower rate at an earlier stage (e.g. before 6:30) such as once every 1, 5, 10 or 15 minutes) and at a higher rate at a later stage (e.g., between 6:30 and 7:30) such as every 1, 10, 15, 30 or 60 seconds. The rates can also be much larger or smaller than the given examples. The user interface may also be capable of displaying the "sleep log" of the user, i.e., display a hypnogram of the night's (or nights') sleep.

If EEG is used to detect the sleep stages of the user, the user convenience may be improved by using so called dry EEG sensors. The sleep stage sensing may also be implemented in different ways. One way is to use a heart rate sensor, which is worn as a chest band or a wristband. One way to measure the depth of sleep is to measure the jitter of the heart rate (i.e., the variations in the time intervals between consecutive heart beats). Other characteristics of the pulse or heart rate may also be used to determine the depth of sleep. Another way would be to measure the blood pressure of the user; it is known from prior art that sleep affects the blood pressure. Another way would be to use body temperature sensors. It is known that the body temperature of a human may drift slightly during REM sleep. Skin resistance sensors may also be used to measure the amount of sweat on the users skin. The aforementioned temperature variations during sleep may cause e.g., some sweating at or after a transition from REM to stage 1 sleep. EMG measuring may also be used (e.g., in combination with EEG measuring) to detect REM sleep. So-called "sleep mattresses," also known as static charge sensitive beds (SCSB), are available too. They are mattresses or sheet-like measurement devices, which are capable of measuring characteristics of sleep and other body functions when a user lies upon the mattress or device. It is also possible to combine several of these measuring techniques and use these data separately or in combination to determine the sleep stage of the user.

One further development of the invention is to determine or approximate the amount of sleep debt in minutes or hours. This approximated amount may then be displayed to the user. For example, the device could determine the ratio between deep sleep and shallow sleep and determine whether the user has had enough of sleep on the basis of this. It is known that sleep debt causes a human to sleep more deeply; i.e., the sleep stages of deep sleep are longer than usually. The REM stages are often correspondingly shorter. (Normally, the deep sleep stages are shorter towards the end of the night. However, when a human is suffering from sleep debt, the last deep sleep stages may be significantly longer than normally.) This sleep characteristic could be used to determine when the user has had enough of sleep. On the basis of the "deep sleep"/"shallow sleep"-ratio, the device could determine whether there is a need to sleep more or not. This could be exploited for a "weekend wake up"-alarm functionality, wherein the user is woken up when he/she has had enough of sleep. There is actually a need for this because sleeping too long also causes a human to feel tired, possibly for the whole day. For example, if the user knows he/she is sleep deprived, he/she can set the alarm clock to alarm between 8 and 11 on Saturday morning (when the device detects that the user has had enough of sleep and is no longer sleep deprived). In this way the user can make sure that he/she gets enough of sleep and thus gets rid of the sleep debt but at the same time he/she can make sure that he/she will not sleep too long and feel drowsy because of that.

The device may also have a separate vibrating alarm device. For example if the sensor unit is worn on the head or chest, the vibrating alarm may be arranged in a wristband wirelessly coupled to the sensor unit and/or central unit. In this way the user can be conveniently woken up without the risk of waking up his/her spouse.

One additional feature of the apparatus could be a so-called snore guard, i.e., a device that monitors the snoring of the user with a microphone and stimulates the user slightly when snoring occurs with sound or vibration until the snoring ceases. The microphone could be placed e.g., on the sensor unit headband. Alternatively, the sensor could monitor the snoring and send a stimulation signal to the sensor unit, which then vibrates. If a mobile phone is used as the central unit, it is quite natural to use the microphone of the mobile phone.

A further additional feature of the device could be a system for estimating the endocrinological (i.e., hormonal) or physiological circadian cycle of the user. It is known that the hormone levels of a human affect his/her alertness and susceptibility to fall asleep. It is known that people are often susceptible to fall asleep easily in early afternoon. (It is often believed that this afternoon drowsiness is caused by a heavy lunch but this belief is at least partly incorrect.) The drowsiness is actually caused by a physiological/hormonal state, which occurs daily and makes the human susceptible to take a nap. Similarly it is known that the level of a certain hormone that makes the human more alert is high during the last hour before the regular time to go asleep for a certain human. That is, if a person goes to sleep at 22:00 every night, the level of this hormone is elevated between 21:00 and 22:00, These physiological/hormonal phenomena occurring recurrently every day (corresponding to the circadian cycle of the person) can be estimated by a mathematical model. The sleep-wake history of the user can be monitored by the sensor unit and central unit and a mathematical model of the users circadian cycle can be created and maintained. The model can then be used to estimate times of physiologically/hormonally suitable intervals to take a nap or fall asleep. Correspondingly, intervals during which falling asleep is less probable can also be predicted. This information can then be presented to the user by a "Now is a suitable time to take a nap"-statement or "It is currently more difficult to fall asleep"-message. The length of the circadian cycle varies from person to person. The natural individual circadian cycle of a person may be slightly more or slightly less than 24 hours. By estimating the length of this individual circadian cycle on the basis of sleep/wake-history, the physiological/hormonal phenomena may be estimated (on the basis of research information regarding the time of occurrence of these phenomena related to e.g. when the individual has woken up).

The invention makes the earlier solutions more convenient to use and especially more convenient to take along when travelling. The invention also makes natural alarm clock products less complex (and thus cheaper), since some of the functionalities are implemented in the mobile terminal.

The invention also provides a user with means to manage his/her sleep better than prior art solutions. The user can make sure he/she gets a suitable amount of sleep, i.e., enough to get rid of sleep debt but not too much to avoid drowsiness caused by that. In addition the invention may estimate suitable and/or unsuitable times to take a nap or go to sleep and thus provide the user with means to understand his/her bodily functions better and thereby adapt his her timetable, naps, and sleep accordingly. Snore guard functionality additionally provides the user with a way to reduce snoring and/or sleep apnea, thus improving his/her quality of sleep and consequently improve quality of life.

Basically, the goal is to satisfy the customers' need to wake up pleasantly with a feeling of mental alertness and without drowsiness. It appears to be much more pleasant to wake up between sleep cycles than in the middle of a sleep cycle. People are usually much drowsier when they are waked up by an alarm clock than when they wake up naturally without an alarm clock.

According to some studies, the length of sleep is not what causes us to be refreshed upon waking. The key factor is the number of complete sleep cycles we enjoy. Each sleep cycle contains five distinct phases, which exhibit different brainwave patterns. For our purposes, it suffices to say that one sleep cycle lasts an average of 90 minutes: 65 minutes of normal, or non-REM (rapid eye movement), sleep; 20 minutes of REM sleep (in which we dream); and a final 5 minutes of non-REM sleep. The REM sleep phases are shorter during earlier cycles (less that 20 minutes) and longer during later ones (more than 20 minutes). According to the same study, if we were to sleep completely naturally, with no alarm clocks or other sleep disturbances, we would wake up, on the average, after a multiple of 90 minutes—for example, after 4½ hours, 6 hours, 7½ hours, or 9 hours, but not after 7 or 8 hours, which are not multiples of 90 minutes. In the period between cycles we are not actually sleeping: it is a sort of twilight zone from which, if we are not disturbed (by light, cold, a full bladder, noise), we move into another 90-minute cycle. A person who sleeps only four cycles (6 hours) will feel more rested than someone who has slept for 8 to 10 hours but who has not been allowed to complete any one cycle because of being awakened before it was completed. A user can thus keep a sleep journal. Record the beginning and waking times for each natural sleep episode that is uninterrupted by an alarm or any other disturbance. Find the common multiple. For example, if your recorded sleep periods were 400, 500, 400, 200, and 700 minutes, you would conclude that your personal sleep cycle typically lasts for 100 minutes, or 1⅔ hours. Once the user knows the length of a typical sleep cycle, then, where possible, the user can plan his or her waking accordingly. The author of this study mentions that: "If I am ready for bed at 11:00 p.m. and I know that I must rise at 6:00 a.m. in order to make a 7:00 breakfast meeting, I read for about 45 minutes to avoid the alarm going off during the last half of my cycle."

According to another study, sleep inertia is a transitional state of lowered arousal occurring immediately after awakening from sleep and producing a temporary decrement in subsequent performance. Many factors are involved in the characteristics of sleep inertia. The duration of prior sleep can influence the severity of subsequent sleep inertia. Although most studies have focused on sleep inertia after short naps, its effects can be shown after a normal 8-h sleep period. One of the most critical factors is the sleep stage prior to awakening. Abrupt awakening during a slow wave sleep (SWS) episode produces more sleep inertia than awakening in stage 1 or 2, REM sleep being intermediate. Therefore, prior sleep deprivation may enhance sleep inertia since it increases SWS. There is no direct evidence that sleep inertia exhibits a circadian rhythm. However, it seems that sleep inertia is more intense when awakening occurs near the trough of the core body temperature as compared to its circadian peak. A more controversial issue concerns the time course of sleep inertia. Depending on the studies, it can last from 1 min to 4 h. However, in the absence of major sleep deprivation, the duration of sleep inertia rarely exceeds 30 min. But all these results should be analysed as a function of type of task and dependent variables. Different cognitive functions are probably not sensitive to the same degree to sleep inertia and special attention should be provided to dependent variables as a result of the cognitive processes under review. Finally, sleep disorders represent risk factors which deserve new insight in treatment strategies to counteract the adverse effects of sleep inertia.

The present idea is basically to let the user set a time interval during which he would like to wake up. The Natural Alarm Clock then monitors the user's sleep phases and wakes him up at a natural stage of sleep within the set time interval. If a natural time for the alarm cannot be set within the set time interval, the alarm goes off at the end of the time interval.

The product is a combination of a mobile enhancement and a software program for a mobile phone. The mobile enhancement is, e.g., a "sweatband", which is worn on the head of the user. The sweatband includes sensors and a bluetooth chip. The sensors measure the brain activity of the user and send the data over a bluetooth connection to the mobile phone. The mobile phone computes the current sleep phase, detects the sleep cycles and sounds the alarm at a time when it is pleasant and easy for the user to wake up (within the time interval set by the user). Preferably, the product would also adapt its mathematical model of sleep phases and sleep cycles to the observed sleep patterns of the user.

The present invention can be further appreciated with reference to the accompanying figures. FIG. 1(a) shows the different sleep stages and the related terminology. The shallowest stage is REM (rapid eye movement) sleep 101, which is when dreaming occurs. The rest of the cycle is NREM (non-rapid eye movement). The shallowest stage of NREM is Stage 1 sleep 103, followed by Stage 2 sleep 105. The deepest NREM sleep stages are stage 3 107 and stage 4 109. The term slow wave sleep (SWS) may be used to denote stage 3 and stage 4 sleep.

The term "sleep cycle" refers generally to a period of sleep which includes the following series of sleep stages: Stage 1→Stage 2→Stage 3→Stage 4→Stage 3→Stage 2→Stage 1→REM→Stage 1. A sleep cycle may, however, lack some of the stages in this sequence. A transition from REM to stage 2 or vice versa, without a phase of stage 1 sleep, is quite common. A sleep cycle may also lack stage 4 or SWS altogether, which typically occurs at a late stage of the night, i.e., after about 4 hours of sleep. It is also possible to awaken from any stage as a result of outer stimuli or without any apparent cause. Microarousals, or brief transitions to a shallower sleep stage or wakefulness and back again, are possible.

Figure 1B:
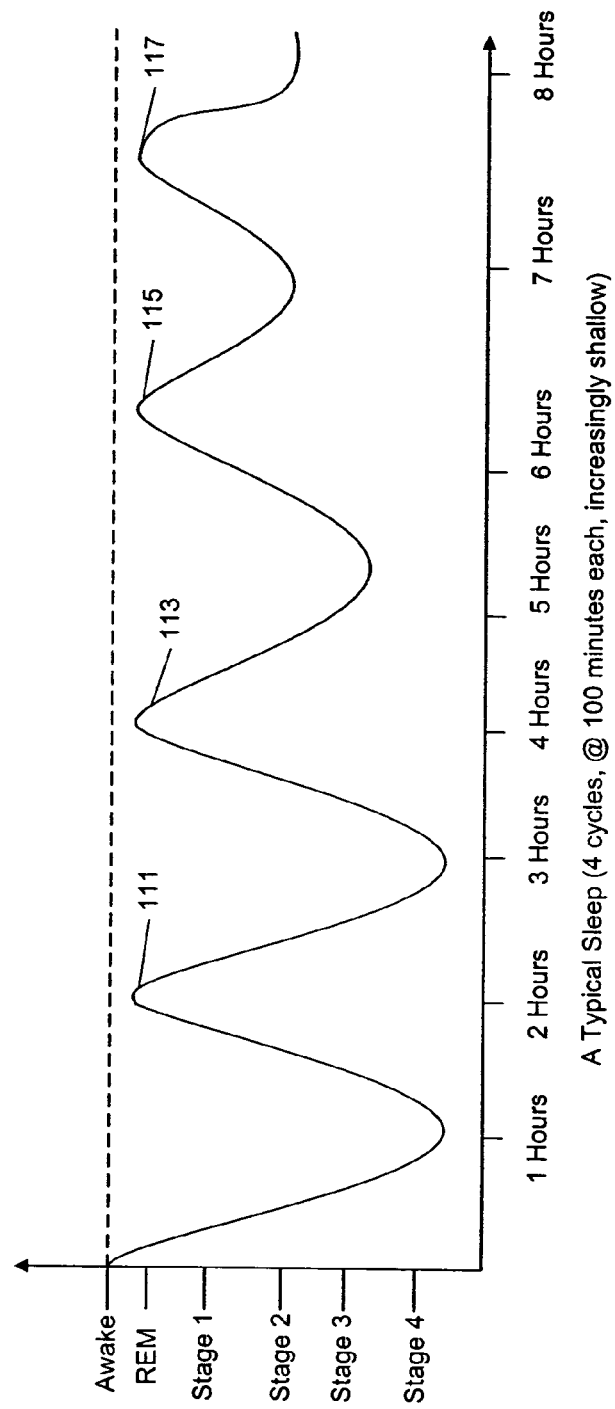
FIG. 1(b) graphically shows a generalized representation of a typical person's night of sleep.

As seen in FIG. 1(b), a person typically experiences about four cycles of sleep per night, lasting about 100 minutes each. The later cycles do not include SWS sleep. The opportune times to wake a person up would be during REM sleep at points 111, 113, 115, and 117 or in NREM sleep near the transition from REM to NREM. The FIG. 1(b) is a rough generalization, and actual sleep patterns may differ significantly from the pattern presented in the figure.

Figure 2:
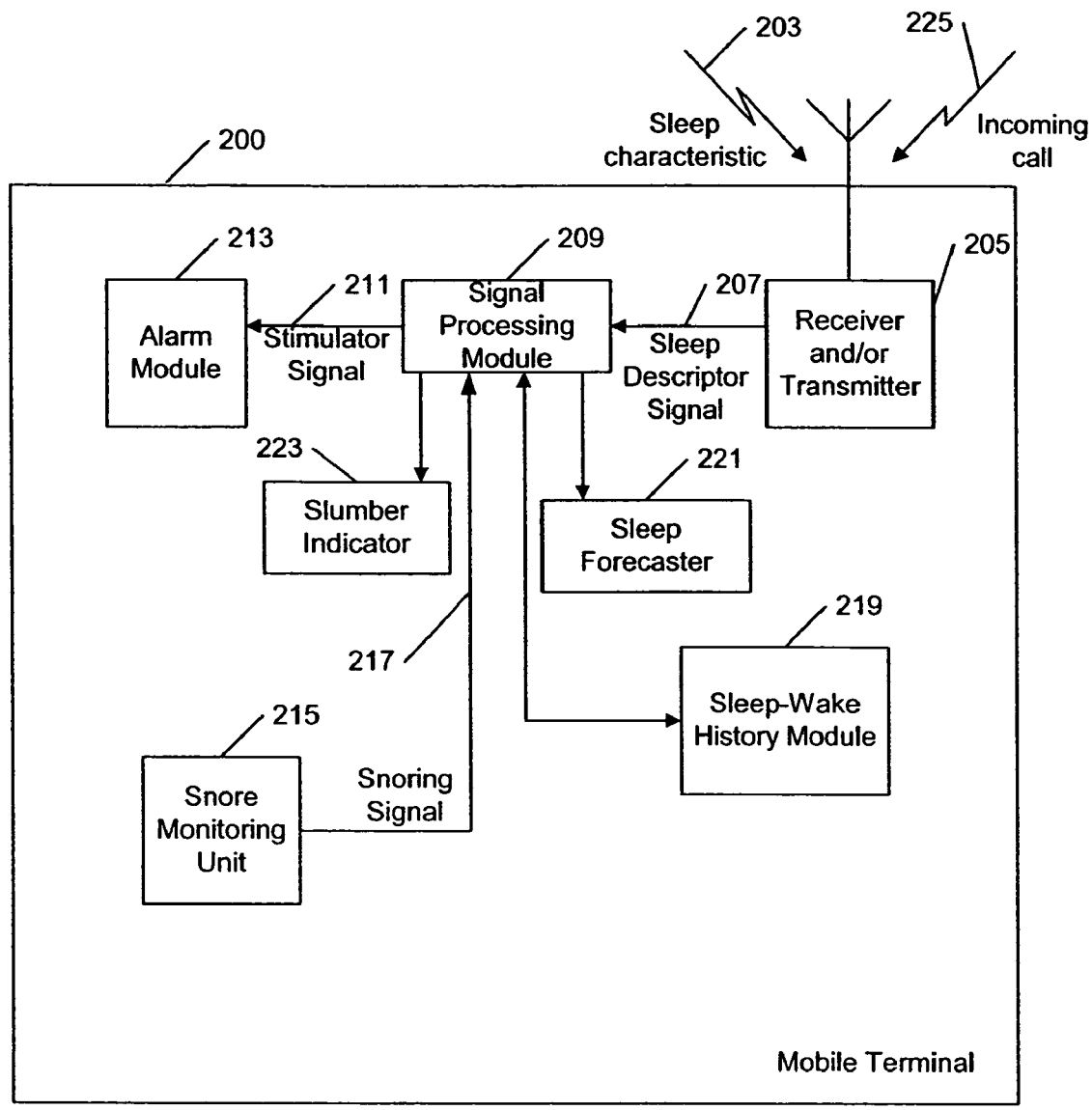
FIG. 2 shows is a block diagram of a mobile terminal according to an embodiment of the present invention.

Referring now to FIG. 2, a mobile terminal 200 is shown according to an embodiment of the present invention. An awakening module such as alarm module 213 is for bringing the user closer to an awake state, which may involve totally waking up the user, or only causing the user's sleep to become more shallow NREM sleep, or both. A sleep characteristic 203 arrives at a transceiver 205, which then conveys a sleep descriptor signal 207 to a signal processing module 209. The signal processing module 209 uses this sleep information to determine if the user should be awoken, for example if it is past 6:00 AM and the sleep information indicates the user is at or near a transition from REM to NREM. In that case, the signal processing module sends a stimulator signal 211 to the alarm module 213 which may emit a gradually increasing level of decibels in order to wake the user up (this stimulator signal is also referred to herein as a stimulation signal). Alternatively, the stimulator signal 211 may be sent to the transmitter 205 for transmission to a device containing a vibrating alarm module. A vibrating alarm may be preferable in order to prevent other people (such as a spouse) from being awoken. Such a vibrating alarm could be worn by a person, or it could be integrated with a pillow, for example.

This mobile terminal 200 also includes a snore monitoring unit 215 which may include a microphone for detecting whether the person is snoring loudly. If so, then a snoring signal 217 is sent to the signal processing module 209, which determines an appropriate stimulus for ending the snoring, and the alarm module 213 accordingly provides that stimulus. Or, as noted above, a vibrating alarm can be used instead of the audio alarm 213.

This mobile terminal 200 further includes s sleep-wake history module 219 that interacts with the signal processing module 209 in order to maintain a record of sleeping habits and sleeping data, which can enable the mobile terminal to make recommendations to the user about when would be a good time to take a nap, and can also enable the terminal to more accurately estimate when the user will next reach REM. The sleep forecaster 221 can provide that estimate to another person, such as a person trying to reach the user by telephone or email, or a person in the same room with the sleeper. Such a person may simply be provided with information about the user's current sleep stage, instead of or in addition to an REM forecast, and that sleep stage information may be provided by a slumber indicator 223. The Slumber indicator may, for example, provide information to known presence services. The slumber indicator may notify a server over SIP (Session Initiation Protocol) when the user falls asleep.

In addition to responding to a sleep characteristic 203, this mobile terminal is also able to respond to an incoming call (or email or other message) 225, for example by waking up the user if the user is in a suitable stage of sleep, or instead leaving an urgent message that will automatically wake up the user when the user reaches a transition from REM to NREM. This way, the user will be able to respond to the incoming call 225 with a clear head, even if it is the middle of the night.

Figure 3:
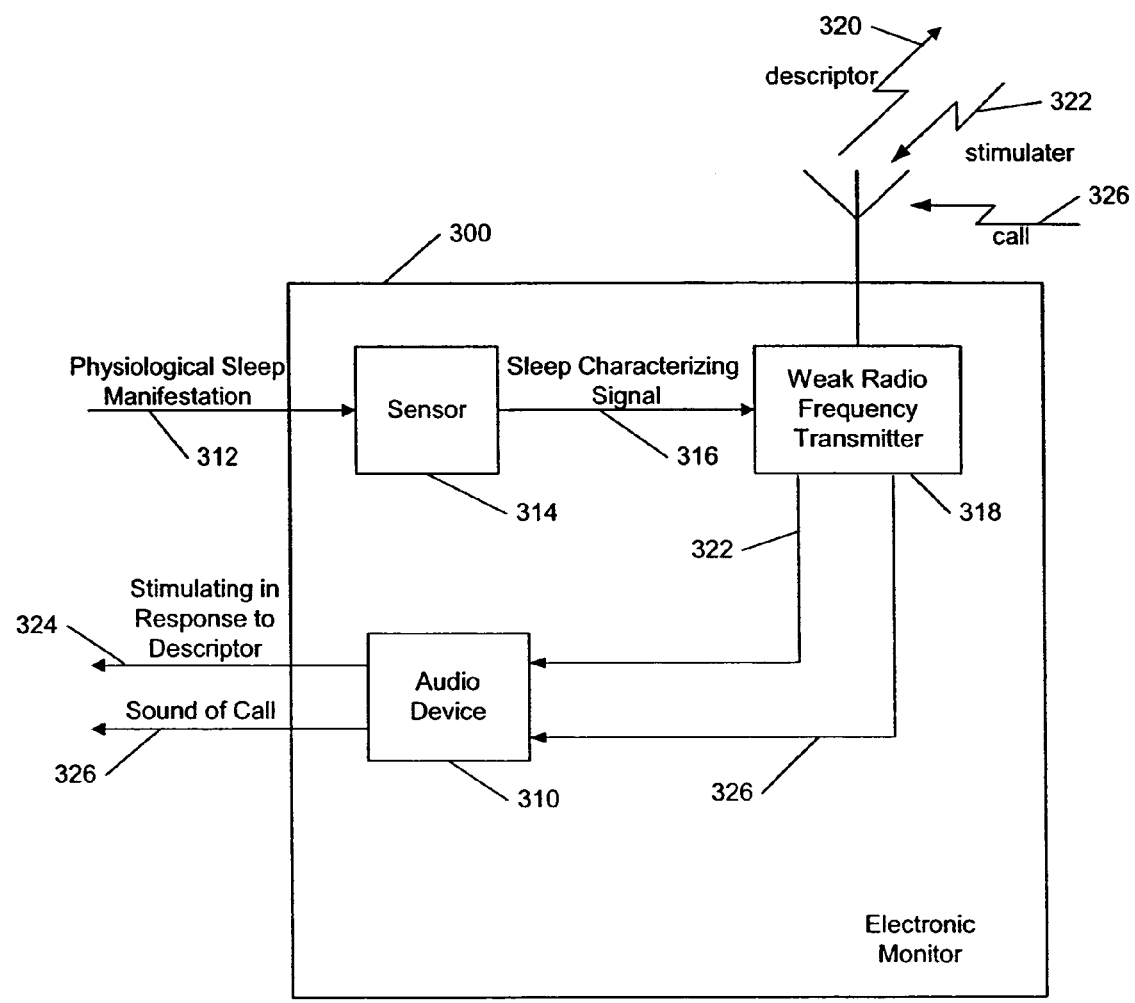
FIG. 3 is a block diagram of an electronic monitor according to an embodiment of the present invention.

Referring now to FIG. 3, this drawing shows an electronic monitor 300 according to an embodiment of the present invention. This monitor is also equipped with a stimulating unit such as a vibrational unit or the audio device 310 for waking up the user. If the audio device is a speaker or loudspeaker instead of a buzzer or bell, then the audio device may serve a dual purpose of also conveying incoming call audio to the user. Additional functions of the audio device 310 are also possible, such as conveying soothing sounds until the user falls asleep. In addition to or instead of the audio device 310, the electronic monitor 300 may include a haptic stimulation device such as a vibrating alarm for waking up or stimulating the user. A physiological sleep manifestation 312 is signaled to a sensor 314 in the electronic monitor. This manifestation may, for example, be the pulse of the user, or some other indicator of REM versus NREM or of sleep depth in general. The sensor 314 may also be an active sensor such as a PPG sensor, which emits light. The sensor then sends a sleep characterizing signal 316 to a weak radio frequency transmitter 318 which sends a descriptor signal 320 to a mobile terminal, for example. The transmitter is weak so that battery power and recharging requirements are minimal, and it transmits in a radio frequency so that a direct line of sight is not required (as it is for infrared signaling). The electronic monitor 300 subsequently may receive a stimulator signal 322 instructing that the sleeping person be stimulated toward an awake state (e.g. woken up), and this stimulator signal is conveyed to the audio device 310 and/or vibrator device, which then provides the stimulation 324. Subsequently, the audio device 310 may also be able to convey to an awake user the sound of a call 326.

Figure 4:
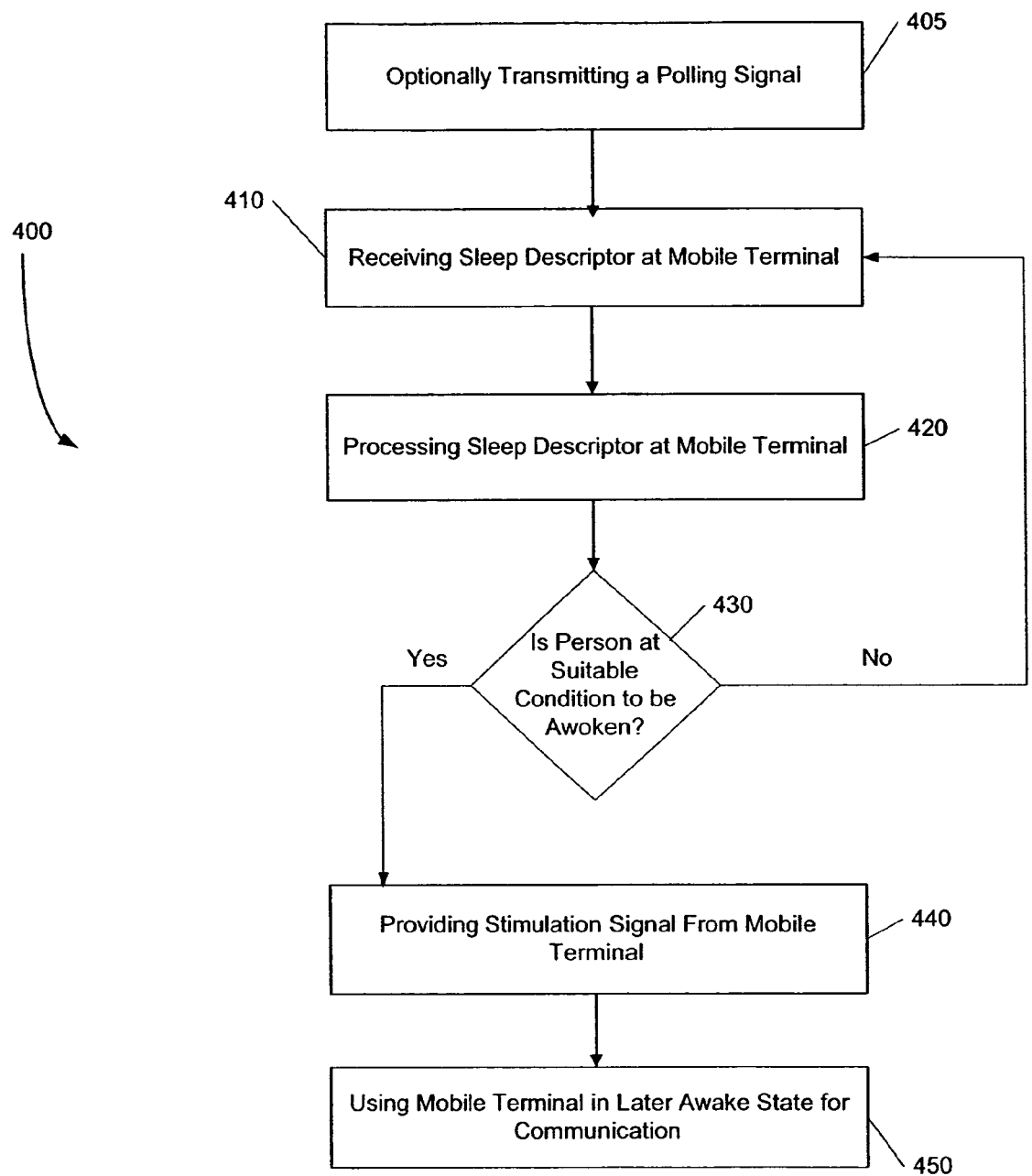
FIG. 4 is a flow chart of a method according to the present invention.

Referring now to the flow chart in FIG. 4, this drawing depicts a method 400 according to an embodiment of the present invention. A sleep descriptor is received 410 at the mobile terminal, typically from a sensor worn by the user or otherwise in contact with the user. This step 410 can optionally be prefaced and/or prompted by transmitting 405 a polling signal. The polling signal may be transmitted 405 to the source of sleep descriptor signals, for indicating that a sleep descriptor signal is expected. This polling may, for example, be initiated 5, 10, 15 or 30 minutes prior to a user-established wake-up interval, or 120, 110 or 100 minutes prior to a particular wake up deadline, for example. The source of sleep descriptor signals, for example an electronic monitor, may be arranged to transmit sleep descriptors as a response to receiving a polling signal.

In any event, the sleep descriptor is then processed 420 at the mobile terminal, in order to make a determination 430 regarding whether the person is or is not in a suitable condition of sleep to be awoken. For example, the suitable condition may be the time period shortly after a transition is detected from REM to NREM. The determination may be performed on the basis of a sleep descriptor alone, but additional criteria may be used as well. Previously received sleep descriptors may affect the determination; for example, the variation between sleep descriptors may be calculated and the determination may be based on this variation. A transition from REM to NREM may be determined, for example if sleep descriptors indicating (directly or indirectly through variation calculations) NREM-sleep are received for a certain time after first receiving sleep descriptors indicating (directly or indirectly) REM-sleep, e.g., for a certain time. If in a suitable sleep condition, then the mobile terminal provides 440 a stimulation signal to the user or to a stimulator in contact with the user. The stimulation signal may be, for example, an audible alarm having intensity that may be increased over time. The stimulator may be a device comprising a vibrator or other device producing a haptic, audible and/or visible stimulus as a response to the stimulation signal. The intensity of the stimuli may increase over time. However, if the determination 430 indicates that the user is not in a suitable condition to be awoken, then the mobile terminal waits until the user is in the suitable stage of sleep, and this suitable stage is detected by going back to step 410 which entails receiving a sleep descriptor at the mobile terminal.

Of course, if the method is used as an alarm clock, then the sleep descriptor will not be sent until it is morning near the person's requested wake-up time. The determination may in this case depend partly upon on a stored wake-up interval or deadline. As mentioned, this interval or deadline may be used to initiate the polling signal 405. This polling may, for example, be initiated 5, 10, 15 or 30 minutes prior to a user-established wake-up interval, or 120, 110 or 100 minutes prior to a particular wake up deadline, for example. After the user is awake, then the user is able to later use 450 the same mobile terminal for communication, such as email, or wireless, or other communication via a network.

It is to be understood that all of the present Figures, and the accompanying narrative discussions of embodiments, do not purport to be completely rigorous treatments of the method and system and devices under consideration. A person skilled in the art will understand that the steps and signals of the present application represent general cause-and-effect relationships that do not exclude intermediate interactions of various types, and will further understand that the various steps and structures described in this application can be implemented by a variety of different combinations of hardware and software in various different configurations and sequences which need not be further detailed herein. In the examples described herein, Bluetooth is presented as a bearer for signals transmitted over the air. However, other alternatives are also possible, such as ZigBee radio communications or other short-range transmission methods. In addition, cellular networks or other radio communication technologies and networks may be exploited.

What is claimed is:

1. A mobile terminal, comprising:
   a receiver configured to receive a sleep descriptor signal indicative of at least one sleep characteristic of a user; and
   a signal processing module configured to process said sleep descriptor signal,
   wherein said signal processing module is arranged to provide, at least partly in response to the sleep descriptor signal, a stimulation signal for stimulating a user toward an awake state,
   wherein the mobile terminal is also configured for communication by the user in the awake state, and
   wherein the mobile terminal is configured to handle an incoming call in such a manner as to prevent the user from being awakened, if the at least one sleep characteristic has indicated that the user is in a deep sleep, and otherwise to handle the incoming call in a different manner.

2. The mobile terminal of claim 1, further comprising a slumber indicator for indicating to at least one other person whether the user is awake or in a deep sleep or a shallow sleep, based at least partly on the at least one sleep characteristic.

3. The mobile terminal of claim 1, wherein the signal processing module is arranged for at least one of the following tasks:
   preventing the user from falling into a deep sleep, so that the user remains in a shallow sleep,
   turning off soothing sounds when the user falls from a shallow sleep into a deep sleep, and
   causing room temperature to be adjusted before providing the stimulation signal for awakening the user.

4. The mobile terminal of claim 1, wherein the at least one sleep characteristic is indicative of a transition from rapid eye movement to another sleep stage.

5. The mobile terminal of claim 4, wherein the stimulation signal is provided only within a certain period after the transition from rapid eye movement.

6. The mobile terminal of claim 1, wherein the at least one sleep characteristic is indicative of whether the user is in rapid eye movement.

7. The mobile terminal of claim 6, wherein the stimulation signal is provided only in case the at least one sleep characteristic is indicative of rapid eye movement.

8. The mobile terminal of claim 1, further comprising a user interface for setting a desired wake-up interval or an end point of said interval.

9. An electronic monitor, comprising:
   at least one sensor responsive to at least one physiological manifestation that indicates a characteristic of sleep, the at least one sensor being for providing a sleep characterizing signal; and a transmitter, responsive to the sleep characterizing signal, the transmitter being for providing a sleep descriptor signal to a terminal, a receiver for receiving a stimulation signal, and a stimulating unit, wherein said at least one sensor is also responsive to a polling signal before the transmitter provides the sleep descriptor signal.

10. An electronic monitor according to claim 9, wherein said stimulating unit is a haptic stimulation device.

11. The electronic monitor of claim 9, wherein the at least one sensor includes at least part of a static charge sensitive bed.

12. A system, comprising:

at least one sensor responsive to at least one physiological manifestation that indicates a characteristic of sleep, the at least one sensor being for providing a sleep characterizing signal;

a transmitter, responsive to the sleep characterizing signal, the transmitter being for providing a sleep descriptor signal to the mobile terminal;

a receiver at the mobile terminal for receiving the sleep descriptor signal; and a signal processing module at the mobile terminal for processing said sleep descriptor signal, wherein said signal processing module is arranged to provide, at least partly in response to the sleep descriptor signal, a stimulation signal indicative that a user should be stimulated toward an awake state, wherein the mobile terminal is also usable by the user in the awake state, for communication purposes, and wherein the transmitter is configured to provide the sleep descriptor signal in response to a polling signal from the mobile terminal.

13. A method, comprising:

receiving a sleep descriptor signal indicative of at least one sleep characteristic of a user;

processing said sleep descriptor signal, and providing, at least partly in response to the sleep descriptor signal, a stimulation signal for stimulating the user toward an awake state, wherein the method is performed within a mobile terminal that is also usable for communication by the user in the awake state, and wherein an incoming call is handled in such a manner as to prevent the user from being awakened, if the at least one sleep characteristic has indicated that the user is in a deep, and otherwise handling the incoming call in a different manner.

14. A method, comprising:

receiving a sleep descriptor signal indicative of at least one sleep characteristic of a user;

processing said sleep descriptor signal, and providing, at least partly in response to the sleep descriptor signal, a stimulation signal for stimulating the user toward an awake state, wherein the method is performed within a mobile terminal that is also usable for communication by the user in the awake state, further comprising transmitting a polling signal before said receiving of the sleep descriptor.

15. The method of claim 14, also comprising:

determining on at least two instants in time whether the user is in rapid eye movement sleep or NREM rapid eye movement sleep on the basis of at least one of said received sleep descriptor signal, storing determination information regarding an outcome of said determining, detecting a transition from rapid eye movement rapid eye movement sleep to non-rapid eye movement sleep based upon said determination information, and providing said stimulation signal as a response to said detecting.

16. The method of claim 13, also comprising indicating to at least one other person whether the user is awake or in a deep sleep or a shallow sleep, based at least partly on the at least one sleep characteristic.

17. A method for determining when a user should be stimulated toward an awake state, comprising:

receiving a sleep descriptor signal indicative of at least one sleep characteristic of the user;

processing said sleep descriptor signal, and providing, at least partly in response to the sleep descriptor signal, a stimulation signal, wherein the method is performed within a mobile terminal that is also usable for communication by the user in the awake state, further comprising providing to at least one other person an estimated time until the user will arrive at a suitable awakening point, based at least partly on the at least one sleep characteristic.

18. The method of claim 14, wherein the processing is for doing at least one of the following tasks:

preventing the user from falling into a deep sleep, so that the user remains in a shallow sleep, turning off soothing sounds when the user falls from a shallow sleep into a deep sleep, and causing room temperature to be adjusted before providing the stimulation signal for awakening the user.

19. A computer-readable medium, the medium being encoded with a software data structure for performing the method of claim 13.

20. A computer-readable medium, the medium being encoded with a software data structure for performing the method of claim 14.

21. The computer-readable medium of claim 19, further comprising software for:

determining on at least two instants in time whether the user is in rapid eye movement sleep or non-rapid eye movement sleep on the basis of at least one of said received sleep descriptor signal, storing determination information regarding an outcome of said determining step, detecting a transition from rapid eye movement sleep to non-rapid eye movement sleep based upon said determination information, and providing said stimulation signal as a response to said detecting step.

22. The method of claim 14, wherein the polling signal is for indicating that a sleep descriptor signal is expected, and the sleep descriptor signal is in response to the polling signal.

23. A mobile terminal, comprising:

means for receiving a sleep descriptor signal indicative of at least one sleep characteristic of the user; and means for processing said sleep descriptor signal, wherein said means for processing is arranged to provide, at least partly in response to the sleep descriptor signal, a stimulation signal for stimulating a user toward an awake state, wherein the mobile terminal is also configured for communication by the user in the awake state, and wherein the mobile terminal is configured to handle an incoming call in such a manner as to prevent the user from being awakened, if the at least one sleep characteristic has indicated that the user is in a deep sleep, and otherwise to handle the incoming call in a different manner.

24. The mobile terminal of claim 23, further means for indicating whether the user is awake or in a deep sleep or a shallow sleep, based at least partly on the at least one sleep characteristic.

25. The system of claim 12, wherein the mobile terminal is also configured to handle an incoming call in such a manner as to prevent the user from being awakened, if the at least one sleep characteristic has indicated that the user is in a deep sleep, and otherwise to handle the incoming call in a different manner.

* * * * *